United States Patent

Takahara et al.

[11] Patent Number: 5,898,077
[45] Date of Patent: Apr. 27, 1999

[54] PROCESS FOR PREPARATION OF AN ESTER

[75] Inventors: Ichiro Takahara; Masumi Kadobayashi; Noriaki Kaminaka, all of Osaka, Japan

[73] Assignee: Matsumoto Yushi-Seiyaku Co., Ltd., Osaka, Japan

[21] Appl. No.: 08/944,549

[22] Filed: Oct. 7, 1997

[51] Int. Cl.$^6$ ..................................................... C07C 51/00
[52] U.S. Cl. ............................................................ 554/167
[58] Field of Search ............................................. 554/167

[56] References Cited

U.S. PATENT DOCUMENTS 4,526,725   7/1985   Deardorff .
5,324,853   6/1994   Jones et al. .

*Primary Examiner*—Samuel Barts
*Attorney, Agent, or Firm*—Birch, Stewart, Kolasch & Birch, LLP

[57] ABSTRACT

The present invention provides a process for preparing an ester comprising the step of reacting a carboxylic acid and an alcohol in the presence of an esterifying catalyst comprising at least one compound having the formula:
$O=M(RCOO)_2$ wherein M represents Sn or Zn and R represents a saturated or unsaturated hydrocarbon group having 1–21 carbon atoms with or without side chains. According to the present process, substantially equal equivalents of the alcohol and the acid can be reacted completely. In addition, the present invention further provides a purification process to eliminate the catalyst from a homogeneous reaction system completely.

6 Claims, No Drawings

PROCESS FOR PREPARATION OF AN ESTER

FIELD OF THE INVENTION

The present invention relates to a process for preparing an ester. In particular, the present invention provides a process that includes a novel step of synthesizing an organic ester by reacting a carboxylic acid and an alcohol under presence of a specified oxy dicarboxylate catalyst of tin or zinc.

DESCRIPTION OF THE PRIOR ART

Numerous esters are synthesized from carboxylic acids and alcohols, and are known to be useful in various fields. In addition, esters derived from natural products are used as, for example, oil, fats or flavors.

Formerly, ester-synthesizing processes had been developed for the purpose of producing natural esters and played an important role in the development of chemical industry. Recently, such processes have been turned to synthesize novel compounds, and numerous valuable materials have been developed.

As for the preparation of an ester, a lot of protocols are known in the art and the most convenient, cost saving and widely applicable process is that comprises dehydration between a carboxylic acid or its anhydride and an alcohol. In the reaction, an acid catalyst, such as sulfate, para-toluene sulfonic acid and a metal oxide, is usually used to cause the reaction to proceed.

A strong acid catalyst, such as sulfonic acid or para-toluene sulfonate, brings various side reactions, for example, dehydration of the alcohol, which provides side products such as olefins or ethers, and the reaction between sulfonic acid, and the alcohol that provides sulfate ester.

When a relatively weak acid, such as a metal oxide, for example titanium oxide, was used as a catalyst, such side reactions could be suppressed but its catalytic activity was not enough. In order to achieve a good yield, the equilibrium of the reaction mixture (i.e., equilibrium between the carboxylic acid and the alcohol, and the produced ester) must be shifted toward the product. Thus, an excess quantity of the acid or the alcohol should be reacted with the other and then the unreacted reactant remaining in the product must be eliminated from the product. Since the elimination of the unreacted material is sometimes difficult or impossible, only an ester of low purity could be obtained. Even if elimination of the starting materials can be effected, there are other problems, for example, the elimination process consumes much time and energy and may result in a very low yield; and in addition, it is often difficult to recycle recovered unreacted materials.

JP. A, 62-289236 describes the use of polytitanium-polyol compositions as an esterification catalyst. However, preparation of the catalyst is difficult. In addition, the reaction mixture is required to contain 25% excess of alcohol than acid. JP. B2, 56-27504 describes titanium and zirconium alkoxydes as esterification catalysts. However, these catalysts are difficult to eliminate from the product because they form colloids during their decomposition step. JP. A, 3-294243 describes clay type adsorptive compositions containing zirconium, however, such a composition is difficult to prepare. JP. A, 53-94296 describes titanium alkoxylate as a catalyst, however, the catalyst is highly expensive and difficult to decompose and eliminate from the product. JP. A, 4-1156 describes hydroxides of IV group metals including zirconium hydroxide as esterification catalysts. However, these catalysts are very difficult to prepare, require a high acid/alcohol ratio, a high temperature and a long time for reaction, and the resulting esters are generally colored.

U.S. Pat. No. 4,526,725 describes a process for the preparation of a purified ester in which a carboxylic acid and an excess alcohol are reacted in the presence of an alkyltitanium complex as a catalyst, followed by steam distillation of the product to eliminate the unreacted alcohol and convert the titanium residue into an undissolved form, and then filtrate the mixture to as eliminate the participating catalyst.

The instant inventors have previously found that an esterifying catalyst comprising at least one compound selected from the group consisting of halides, nitrates, carboxylates and acetylacetone complexes of metals of the titanium group has a great activity, and therefore, substantially equal equivalent of the alcohol and the acid can be reacted completely to give an ester. As a result, the inventors filed U.S. patent application Ser. No. 08/611,162 on Mar. 5, 1996, the entire contents of which are hereby incorporated by reference. The application does not disclose an esterifying catalyst containing an oxy dicarboxylate of tin or zinc.

SUMMARY OF THE INVENTION

An object of the present invention is to provide a novel process for preparing an ester from a substantially equal equivalents of an alcohol and a carboxylic acid, which is substantially free from side products and which provides the desired ester in a good yield.

Accordingly, the present invention provides a process for preparing an ester, comprising the step of reacting a carboxylic acid and an alcohol in the presence of an esterifying catalyst containing at least one compound having the formula $O=M(RCOO)_2$, wherein M represents Zn or Sn, R represents a saturated or unsaturated hydrocarbon group having 1–21 carbon atoms with or without side chains, and preferably, R represents a cycloaliphatic hydrocarbon group with a side chain.

The esterification activity of the catalyst used in the present invention is very high, and therefore, a substantially equal equivalent of the alcohol to the acid is required for complete esterification of the acid. Accordingly, the present invention further provides a process for the preparation of an ester, comprising the step of reacting a carboxylic acid and an alcohol in the presence of an esterifying catalyst containing at least one compound having the formula $O=M(RCOO)_2$, wherein M represents Zn or Sn, R represents a saturated or unsaturated hydrocarbon group having 1–21 carbon atoms with or without side chains, wherein a chemical equivalent of the alcohol to the carboxylic acid is between about 1.0 to 1.1.

Since the novel catalyst used in the inventive process is dissolved in the mixture of the starting materials (i.e., the carboxylic acid and the alcohol), and in the product (i.e., the ester), it acts as a homogeneous catalyst in the homogeneous reaction system.

According to the present invention, the amount of metal from the catalyst remaining in mixture with resulting ester is very little but, in some cases, such a little amount of the metal can exert a bad influence upon use. However, since the catalyst used in the instant esterification method is novel, a method to eliminate the metal from the resulting ester was not known heretofore in the art. As such, another object of the present invention is to provide a process for preparing a highly purified ester comprising a purification step to eliminate the novel catalyst from the obtained ester product.

The present invention further provides a process for the preparation of an ester comprising reacting a carboxylic acid and an alcohol in the presence of an esterifying agent containing at least one compound having the formula O=M(RCOO)$_2$, wherein M represents Zn or Sn, R represents a saturated or unsaturated hydrocarbon group having 1–21 carbon atoms with or without side chains, and purifying the obtained ester by (1) adding an aqueous solution of a chelating agent in the ester to solubilize a zinc or tin residue into an aqueous phase and (2) separating the aqueous phase from the ester.

DETAILED DESCRIPTION OF THE PRESENT INVENTION

In the present specification, the term "an ester" means an organic ester. The term "carboxylate type chelating agent" means a chelating agent having more than one carboxylate moiety.

According to the present invention, a catalyst comprising an oxy dicarboxylate of tin or zinc is one certain a compound having the formula:

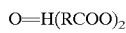

wherein M represents Sn or Zn, R represents a saturated or unsaturated hydrocarbon group having 1–21 carbon atoms with or without side chains, and preferably, R is an aliphatic, cycloaliphatic or aromatic group having 1–21 carbon atoms with or without side chains.

Examples of preferred R group include ethyl, propylene, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicocyl, docosyl, tricocyl, tetracocyl, pentacocyl, isopropyl, tert-butyl, 2-methylpropyl, 2,2'-dimethylpropyl, 3-methylbutyl, 2-ethylhexyl, vinyl, allyl, 2-butenyl, 6-methyl-4-heptenyl, cyclopentyl, cyclohexyl, methylcyclohexyl, ethylcyclohexyl, cyclohexenyl, 1,3-cyclohexadienyl, phenyl, tolyl, cumethyl, benzyl, benzhydryl, phenethyl, tolythyl and naphthyl groups. More preferably, R represents —(CH$_2$)$n$-C$_5$H$_9$ or —(CH$_2$)$n$-C$_6$H$_{11}$(10≦$n$≦20).

Any commercially available compound of the formula can be used in the present inventive process as a novel catalyst. In addition, the catalyst of the present invention can be prepared by any known manner.

In the present invention, the synthesizing step of an ester in the presence of the catalyst specific to the present invention can be practiced by reacting an alcohol and a carboxylic acid in a conventional fashion. For example, the catalyst used in the present invention can be dissolved into the reaction system and the reaction can proceed as a homogenized system. The procedure is described in U.S. patent application Ser. No. 08/611,162 (the patent application is hereby incorporated by reference).

The carboxylic acid reacted with the alcohol according to the present invention may be an aliphatic mono-carboxylic acid, preferably C$_8$–C$_{35}$ fatty acids which may have unsaturated bonds, such as caproic acid, caprylic acid, capric acid, lauric acid, myristic acid, oleic acid and stearic acid; an aliphatic dicarboxylic acid such as maleic anhydride, maleic acid, fumaric acid, adipic acid, sebacic acid and azelaic acid; and aromatic polycarboxylic acid such as phthalic acid, phthalic anhydride, isophtalic acid, trimellitic acid, pyromellitic acid and pyromellitic anhydride; or polymerized carboxylic acid such as polyacrylic acid.

The alcohol reacted with the carboxylic acid according to the present invention is preferably compounds having two or more carbon atoms, one or more hydroxyl group and a boiling point of 120° C. or higher, which may be aliphatic primary alcohols, such as butanol, hexanol, heptanol, octanol, 2-ethylhexanol, decanol, dodecanol and stearyl alcohol; aromatic primary alcohols, such as benzyl alcohol; or polyhydric alcohols, such as ethylene glycol, propylene glycol, neopentyl glycol, trimethylol propane, trimethylol ethane, pentaerythritol, dipentaerythritol, sorbitol and polyvinyl alcohol.

The process of the present application is useful for reacting a higher aliphatic acid and a higher polyhydric alchol, such as polyalkylene glycol, to provide a long chain ester or a polyester having more than one functional group. Especially, the present process is useful for reacting a saturated or unsaturated carboxylic acid having about 5–35 carbon atoms and one or more acid moieties, and an alcohol contains two or more carbon atoms and one or more hydroxyl groups and possesses a boiling point of greater than or equal to about 120° C.

According to the present invention, a chemical equivalent of the alcohol to the carboxylic acid may be about 1.0–1.1. This is a great advantage of the present invention in that a substantially equal equivalent of the alcohol and the carboxylic acid can react almost completely to provide the ester in almost 100% yield within a relatively short period of time.

The amount of the catalyst based on the weight of tin or zinc is preferably between 1 ppm and 5000 ppm, more preferably, between 10 ppm and 1000 ppm by total weight of the carboxylic acid and the alcohol.

The reaction temperature is preferably between 50 and 300° C., more preferably, 120 and 240° C. In case of the carboxylic acid being a polycarboxylic acid such as di- or tricarboxylic acid, more than 200° C. is preferable.

Since the esterification reaction is a reversible one, to remove the produced water from the reaction mixture during the reaction is essential for the process to proceed. The removal of the water can be effected by means of reduced pressure or of a co-boiling agent such as xylene, or the water can be eliminated by bubbling the reaction system with nitrogen gas.

The reaction can be monitored by acid and hydroxyl values of the system. After completion of the reaction, the obtained crude ester may be purified according to a conventional manner. The esterification process of the present invention proceeds in a homogeneous system, the remaining catalyst is dissolved in the resultant ester. To eliminate the catalyst, a solid absorbent agent can be added into the crude product and then the catalyst can be eliminated together with the agent by filtration or centrifugation of the mixture.

Examples of the absorbent agents include active carbonate, synthetic zeolite, natural zeolite, silica-gel, activated clay, activated alumina, charcoal bone, carbon, bauxite, magnesia and flas-earth, and preferably activated carbonate.

In addition to the purification with the assistance of the absorbent agent as above, the residual metal can be eliminated as a water soluble metal complex from the product. According to this purification step, an aqueous solution of a chelating agent is added into the obtained product to form a water soluble metal complex, then the aqueous phase containing the metal can be separated from the ester phase.

Preferably, the chelating agents used in the purifying step are carboxylic acid type chelating agents that able to keep the pH value of their aqueous solution below about 3. Examples of the preferred agents include ethylenediamine tetraacetic acid (EDTA 4H), hydroxy ethylimino diacetic acid, nitlirotriacetic acid, diethylenetriamine penta acetic acid and triethylene tetramine hexa acetic acid and mixtures thereof. In addition, phosphoric acid type chelating agent can also be used in the present invention. Preferable example of the chelating agents includes amino tri(methylene phosphonic acid), 1-hydroxyethylene-1-1-diphosphonic acid, ethylenediamino tetra(methylene phosphonic acid) and diethylenetriamine penta(methylene phosphonic acid).

By means of those chelating agents, the metal atoms in the crude product become free from the carboxylate salts and are dissolved into the aqueous phase. Consequently, by separating the aqueous phase from the obtained ester, the metal can be completely eliminated from the ester product. The ester purified by the present process is free from saponification or coloration, which is a disadvantage of an ester purified with a mineral acid.

According to the present invention, the molar ratio of the chelating agent to the residual metal catalyst existing in the crude ester is preferably more than about 3, more preferably about 3–5.

According to the present invention, the amount of the aqueous solution of the chelating agent may be more than about 5%, preferably about 5–30% by weight of the crude ester.

The purification step of the present invention generally comprising the following sub-steps:

a) Mixing the aqueous solution of the chelating agent to the crude product containing the residual catalyst;
b) Heating the system to form a metal complex of the agent;
c) Allowing the system to stand to allow the aqueous phase to separate from the ester phase;
d) Separating the aqueous phase;
e) Heating the ester phase to eliminate the water remaining in the ester;
f) Filtrating the ester to remove the chelating agent and the metal complex that remains in the product.

The reaction for forming the metal complex may be practiced under atmospheric pressure, at 70–100° C. for 5 minutes–1 hour. Depending on the required purity, the steps a)–f) can be repeated.

The invention will be understood more readily with reference to the following examples; however these examples are intended to illustrate the invention and are not to be construed to limit the scope of the invention.

EXAMPLE 1

Polyethylene glycol (MW=6000) and stearic acid were mixed so that the molar ratio between the hydroxyl group of the alcohol and carboxyl group of the acid being 1:1. A catalyst having the formula:

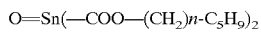

wherein $10 \leq n \leq 20$ (NIKKA-OXTICS: NIHON KAGAKU SANGYOU KABUSHIKI KAISHA, Japan) was added to the mixture to give a catalyst concentration of 0.1% by total weight of the alcohol and the acid. The reaction mixture was heated and reacted at 180° C. for 1 hour, and then at 240° C. for 2 hours. With the progress of the reaction, water was removed through a separator equipped on a reflux condenser. At the end of the reaction, the acid value of the obtained ester was 0.1. Gas chromatography analysis showed that the yield of the ester was 99.5%.

The obtained ester was cooled to 100° C., and 0.05 mole of nitlirotriacetic acid and 15–20% of ion-exchanged water by total weight of the crude ester were added to the ester. The mixture was vigorously stirred at 90–100° C. for 30 minutes. After completion of the reaction, the flask was allowed to stand to allow the aqueous phase to separate from the ester phase. Then, after the aqueous phase was separated from the ester phase and obtained ester phase was washed with the same amount of ion-exchanged water. Next, aqueous phase was separated and the ester was heated at 130° C. to remove remaining water. Gas chromatographic analysis showed the purity of the purified ester was 99.8% and that it contained 0.1 ppm of tin.

EXAMPLE 2

The example 1 was repeated except that a catalyst having the formula:

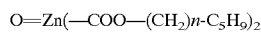

wherein $10 \leq n \leq 20$, was used. The acid value of the obtained crude ester was 0.1 and the yield was 99.7%. The purified ester had a 99.8% purity and contained 0.1 ppm of zinc.

COMPARATIVE EXAMPLE 1

The example 1 was repeated except that a catalyst having the formula:
$O=Ti(-COO-(CH_2)n-C_5H_9)_2$ wherein $10 \leq n \leq 20$, was used. The acid value of the obtained crude ester was 3.0 and the yield was 95%. The purified ester had a 99.8% purity and contained 0.1 ppm of titanium.

What is claimed is:

1. A process for preparing an ester, comprising the step of:
reacting a carboxylic acid and an alcohol in the presence of an esterifying catalyst that comprises at least one compound having the formula $O=M(RCOO)_2$,
wherein M represents Sn or Zn, and R represents a saturated or unsaturated hydrocarbon group having 1–21 carbon atoms with or without side chains.

2. The process of claim 1, wherein R is $-(CH_2)n-C_5H_9$ or $-(CH_2)n-C_6H_{11}$ ($10 \leq n \leq 20$).

3. The process of claim 1, wherein:
said carboxylic acid is a saturated or unsaturated carboxylic acid having about 5–35 carbon atoms and one or more acid moieties, and
said alcohol contains two or more carbon atoms and one or more hydroxyl groups and possesses a boiling point of greater than or equal to about 120° C.

4. The process of claim 1, wherein a chemical equivalent of the alcohol to the carboxylic acid is between about 1.0 and 1.1.

5. The process of claim 1, which process further comprises a purifying step that contains the following sub-steps:
(1) adding an aqueous solution of a chelating agent to the obtained ester to solubilize a Sn or Zn residue into an aqueous phase, and
(2) separating the aqueous phase from the ester.

6. The process of claim 5, wherein said chelating agent is selected from the group consisting of ethylene diamine tetra acetic acid, hydroxyethylimino diacetic acid, nitrilotriacetic acid, diethylenetriamine penta acetic acid, triethylene tetramine hexa acetic acid, and mixtures thereof.

* * * * *